United States Patent

Paap

[11] Patent Number: 4,539,847
[45] Date of Patent: Sep. 10, 1985

[54] ACOUSTIC METHOD AND APPARATUS FOR MEASURING THICKNESS OF A COATING LAYER ON A SUBSTRATE

[75] Inventor: Hans J. Paap, Houston, Tex.

[73] Assignee: Texaco Inc., White Plains, N.Y.

[21] Appl. No.: 567,707

[22] Filed: Jan. 3, 1984

[51] Int. Cl.³ .................................................. G01N 29/00
[52] U.S. Cl. .................................. 73/579; 73/622; 73/638
[58] Field of Search .................. 73/579, 623, 638, 639, 73/588

[56] References Cited

U.S. PATENT DOCUMENTS

| | | | |
|---|---|---|---|
| 3,577,981 | 5/1971 | Kuris | 73/579 |
| 3,872,443 | 3/1975 | Ott | 73/579 |
| 4,128,011 | 12/1978 | Savage | 73/579 |

*Primary Examiner*—Anthony V. Ciarlante
*Attorney, Agent, or Firm*—Robert A. Kulason; Henry C. Dearborn

[57] ABSTRACT

A method or system for measuring thickness of a coating layer on a substrate. It employs acoustic energy and involves transmitting a sweep of frequencies covering a predetermined range through the substrate and its coating. The energies reflected back by the substrate and coating are determined as a function of the frequencies in said range, and the transmission pattern provides a basis for determining the coating thickness.

13 Claims, 10 Drawing Figures

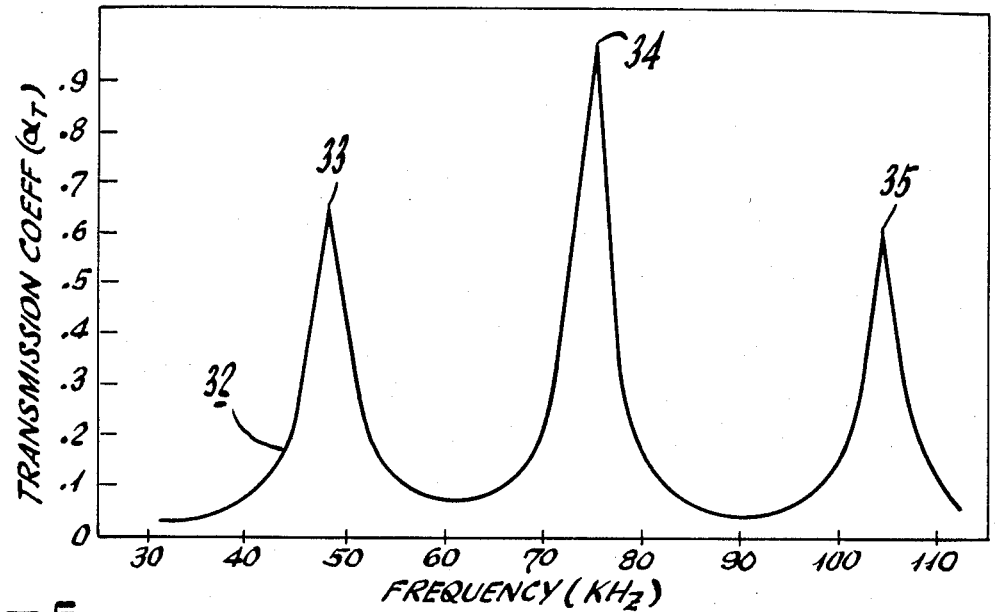
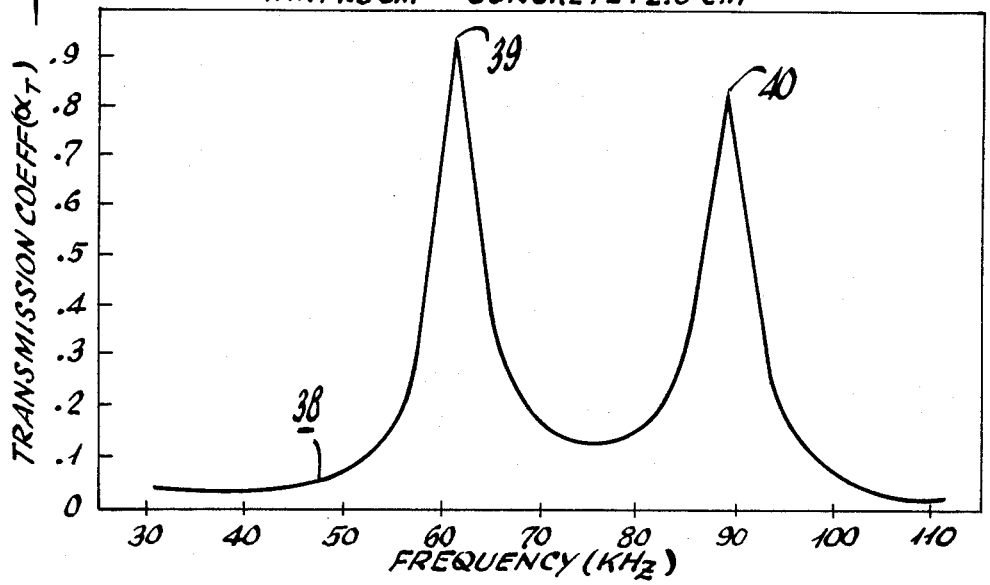
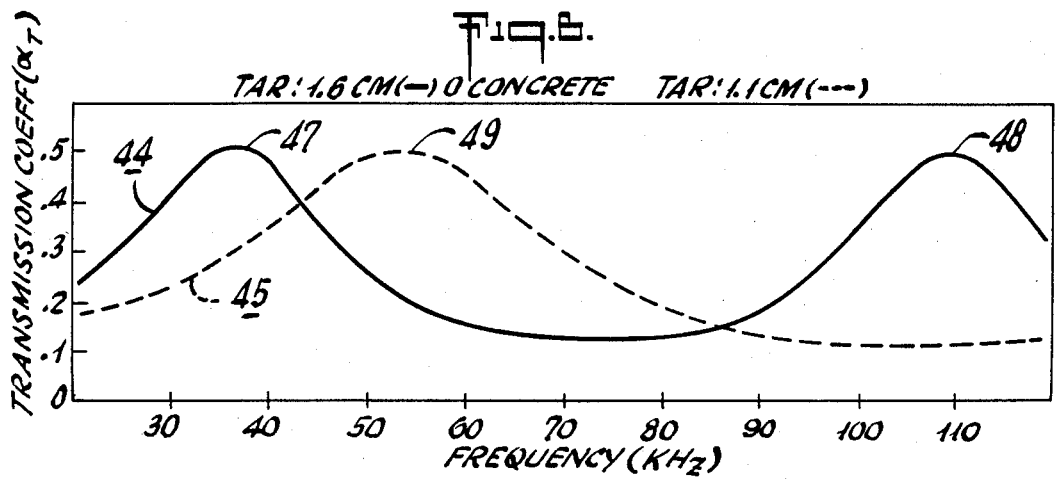

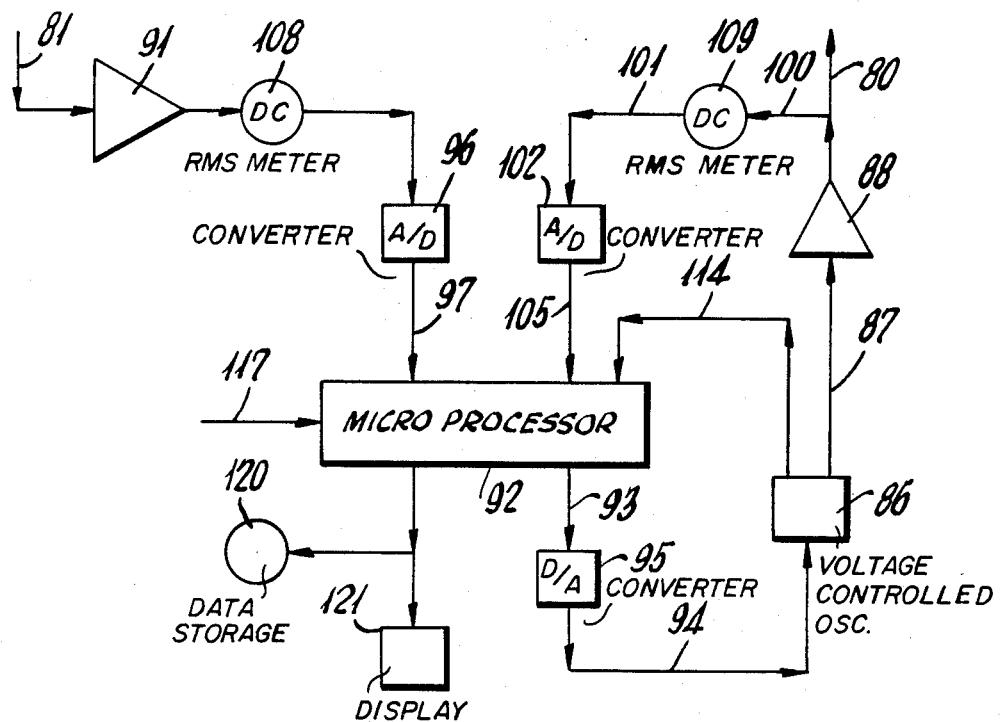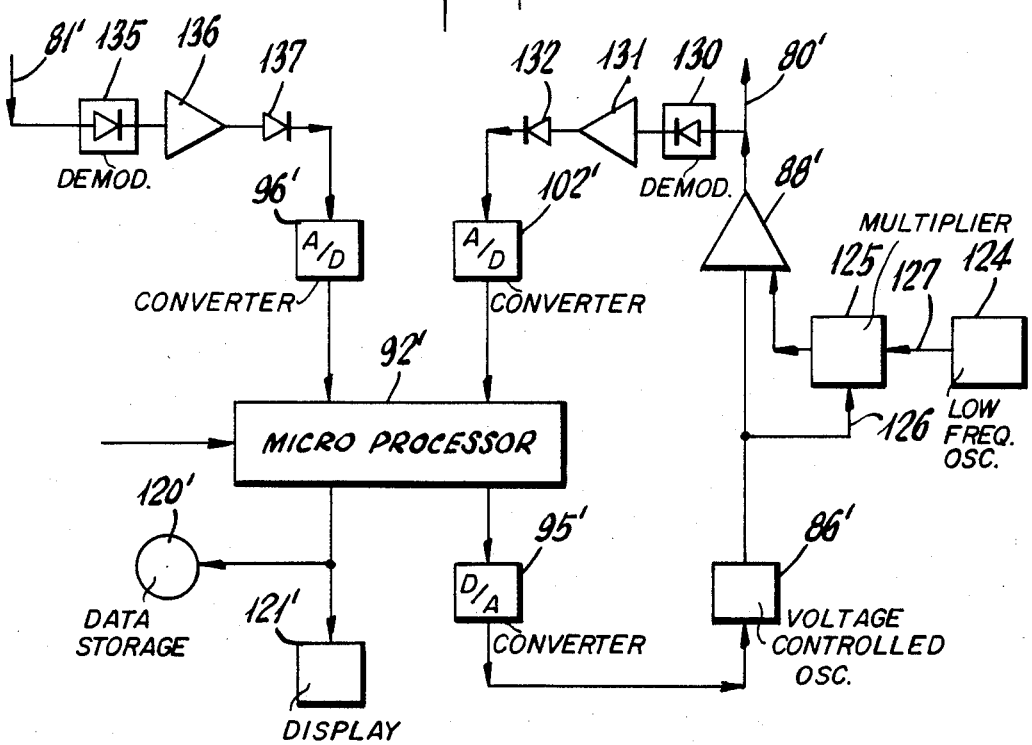

ACOUSTIC METHOD AND APPARATUS FOR MEASURING THICKNESS OF A COATING LAYER ON A SUBSTRATE

BRIEF SUMMARY OF THE INVENTION

This invention concerns an acoustic method and apparatus for measuring thickness of a coating layer on a substrate. More particularly it relates to measuring the thickness of a concrete coating on a subsea pipeline.

Briefly, the invention concerns a method of determining the thickness of a coating layer on a substrate. The method comprises the steps of transmitting acoustic energy through said substrate and coating layer transversely to said coating layer, and sweeping the frequency of said transmitted acoustic energy over a predetermined range of frequencies. It also comprises the steps of receiving reflected acoustic energy from the boundary between said substrate and coating layer and between said coating layer and beyond, and determining the frequencies at which maximum acoustic energy transmission occurs whereby said coating layer thickness may be determined.

Again briefly, the invention concerns a system for determining thickness of a layer of coating on a substrate. It comprises in combination a first piezoelectric transducer for transmitting a range of frequencies 20–120 KHz of acoustic energy through said substrate and said coating, and a voltage controlled variable frequency oscillator and first circuit means for introducing a voltage to sweep said oscillator over said range of frequencies and for connecting said oscillator to energize said first transducer. It also comprises a second piezoelectric transducer for receiving reflections of said transmitted range of acoustic energy and for generating signals in accordance therewith, and second circuit means comprising a microprocessor for determining the amplitude of said reflection signals whereby said coating thickness may be determined from the transmissibility pattern over said frequency range.

Again briefly, the invention concerns a method of measuring thickness of a concrete layer on a subsea pipeline, wherein said pipeline includes a pipe coated with a layer of concrete. The method comprises transmitting a frequency sweep of acoustic energy through a wall of said coated pipe, and receiving reflected acoustic energy returned over said frequency sweep. It also comprises determining the acoustic transmissibility through said wall of coated pipe over said frequency sweep whereby said concrete layer thickness may be determined.

Once more briefly, the invention concerns a system for measuring thickness of a concrete coating on a subsea pipeline. It comprises in combination, a first piezoelectric transducer adapted for transmiting a sweep of acoustic energy over a range of 20–120 KHz through the wall of said pipe and concrete coating into said sea, and a second piezoelectric transducer adapted for receiving said sweep of acoustic energy reflected from the boundaries of said pipe wall and concrete coating. It also comprises first circuit means for energizing said first transducer, and second circuit means for amplifying signals generated by said second transducer. It also comprises a variable frequency oscillator for generating a sweep of frequencies over said range of 20–120 KHz, and third circuit means for connecting the output of said oscillator to said first transducer. It also comprises means for measuring the amplitudes of said transmitted and received acoustic energies, and a microprocessor. It also comprises fourth circuit means for connecting said microprocessor to control said oscillator, and fifth circuit means for connecting said amplitude measuring means to said microprocessor whereby the ratio of said measured amplitudes over said range of frequencies may be determined and the thickness of said concrete coating measured.

When subsea gas and oil gathering and transmission pipelines are laid in hostile offshore environments, they are commonly protected against float-up, fishing vessel trawlboards, marine growth, and the like by employing two to three inch thick coatings of reinforced concrete. The concrete coating is commonly applied over a coal-tar and fiber wrap base of up to five-eighths inch thickness. The coatings are generally designed to result in about 60–70 pounds per foot of negative buoyancy. However, pipe float-up due to loss of concrete coating weight has occurred in at least one instance. Furthermore, environmental safety requirements dictate that such pipelines should be inspected periodically for indications of concrete coating deterioration and/or loss which would signal the danger of float-up and associated break of the pipeline. Such danger is exceptionally great for large diameter high pressure gas lines such as the 36-inch diameter gas pipeline from the Ekofisk field located in the Norwegian sector of the North Sea to Emden, West Germany. That line operates at pressures up to 1,800 psi.

A heretofore proposed method to inspect the integrity of concrete coating of a subsea gas pipeline has been investigated experimentally and by computer simulation vis-a-vis its use in a pipeline pig to determine loss of concrete coating. It involved high intensity neutron sources and the measurement of thermal as well as epithermal neutron fluxes. However, that method exhibited a marginal signal for complete loss of two inches of concrete, and a low signal to noise ratio with respect to variations in gas pressure and sensor-to-pipe-wall separation. In addition, that method required a number of high intensity neutron sources to adequately cover the pipe circumference and this would present an intolerable risk for any personnel handling the pipeline pig which would be used to incorporate the instrumentation.

Consequently, it is an object of this invention to provide a non-nuclear method for measuring the thickness of concrete coating on a subsea pipeline.

Another object of the invention is to provide a system for acoustic measurement of the thickness of a coating layer on a substrate. More particularly, it may be applied to apparatus for surveying the thickness of a concrete coating layer on a subsea pipeline.

BRIEF DESCRIPTION OF THE DRAWINGS

The foregoing and other objects of benefits of the invention will be more fully set forth below in connection with the best mode contemplated by the inventor of carrying out the invention, and in connection with which there are illustrations provided in the drawings, wherein.

Figure 2:
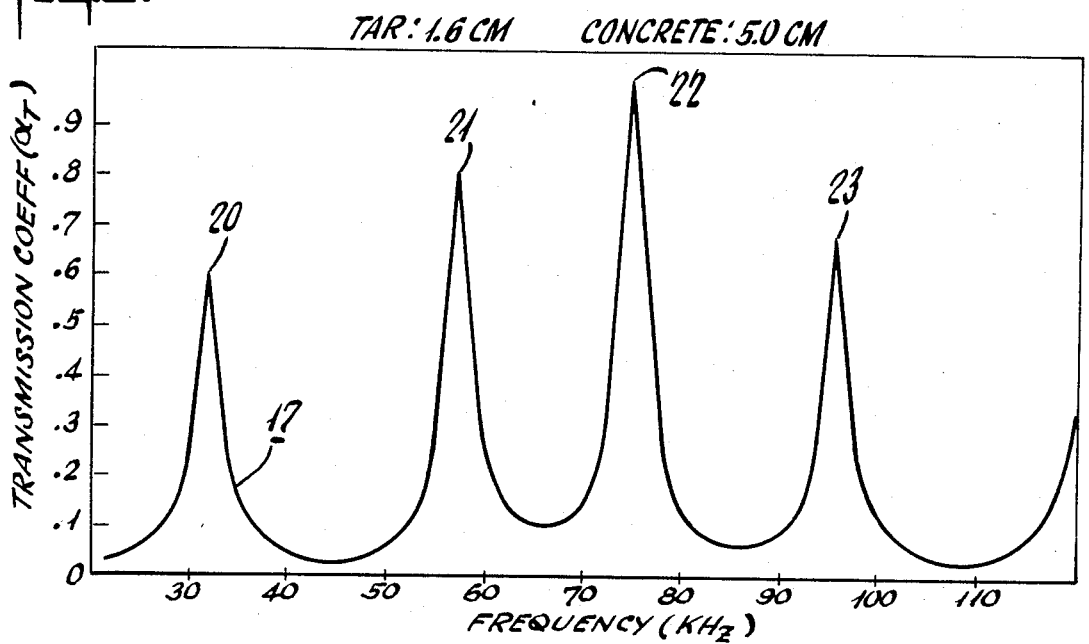
FIG. 2 is a graph illustrating the transmissibility of acoustic plane waves through a coating of concrete 5.0 mm thick over a tar layer of 1.6 cm over the frequency range from 20–120 KHz.
Figure 3:
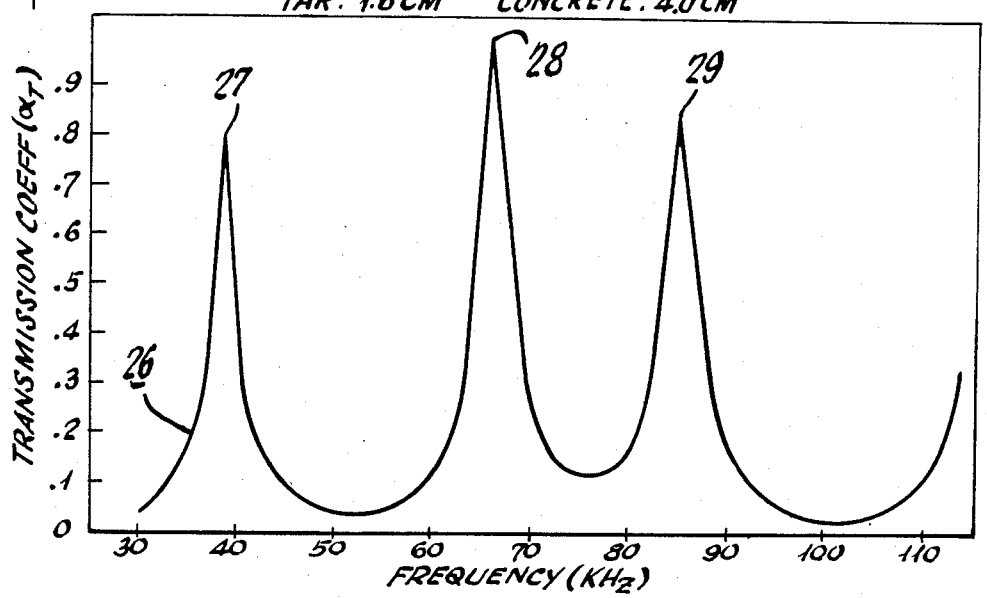
Figure 7:
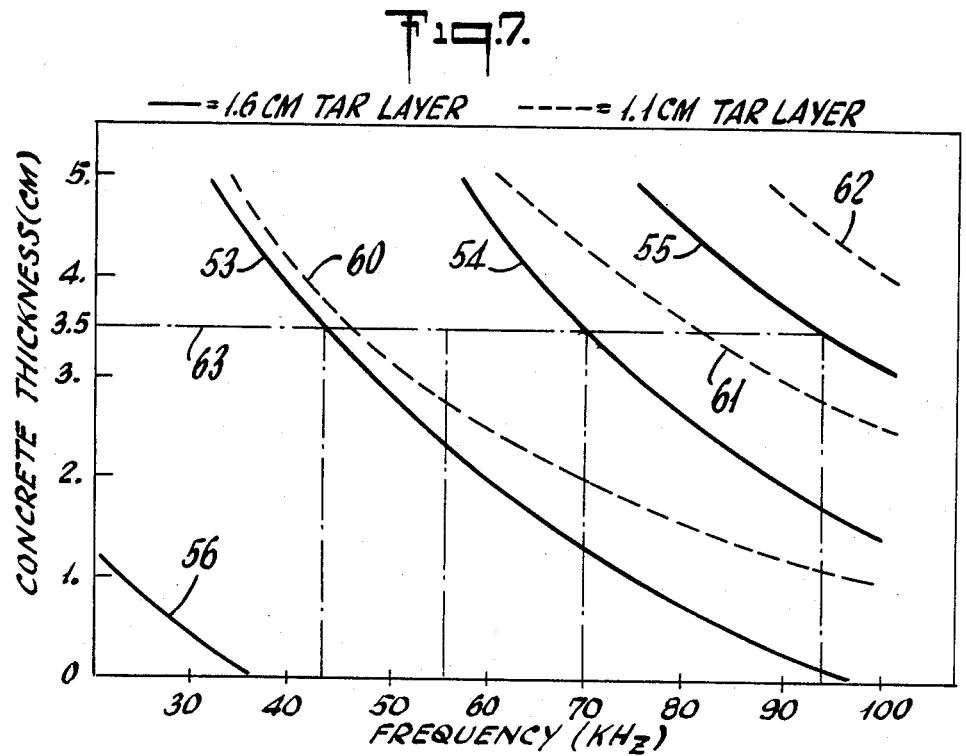
Figure 8:
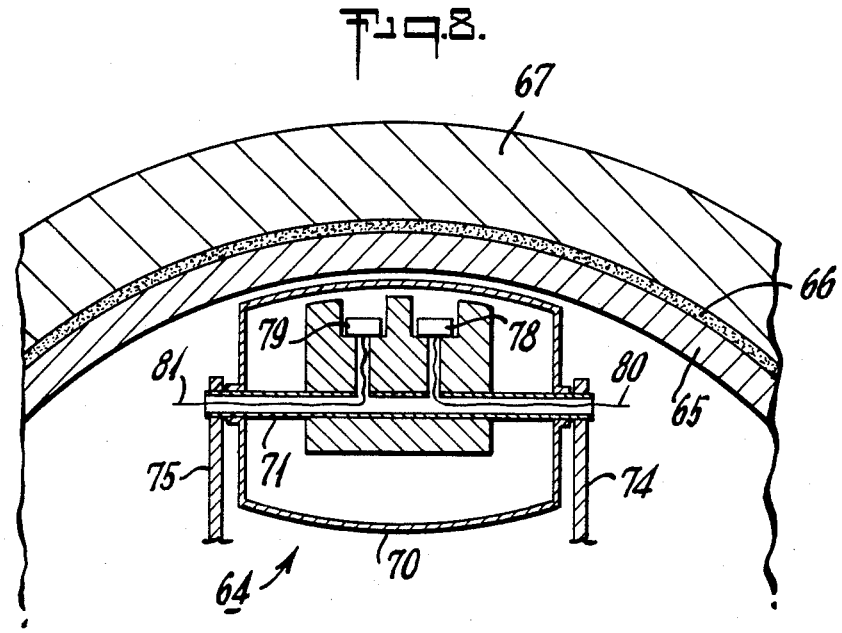

FIGS. 3–5 are similar graphs like FIG. 2 and showing the transmissibility of the coatings as the ordinates with frequency in kilohertz as the abscissas, where the concrete has thicknesses of 4, 3 and 2 cm respectively and the tar thickness remains at 1.6 cm for each;

FIG. 6 is another similar graph showing transmissibility of two tar layer thicknesses with zero concrete thereover, covering the same frequency range as the other graphs;

FIG. 7 is a graph illustrating curves that may be developed for representing the concrete thickness as the ordinate against the frequency as the abscissa for tar thickness layers of 1.6 cm (solid line curves) and 1.1 cm thickness (dashed line curves);

FIG. 8 is a schematic cross sectional illustration indicating a pipeline probe adjacent to the inside surface of the pipe;

FIG. 9 is a schematic block diagram illustrating the elements of an electrical system which may be employed to carry out a procedure according to the invention; and FIG. 10 is another schematic block diagram illustrating a modification of the system illustrated in FIG. 9.

DETAILED DESCRIPTION

Figure 1:
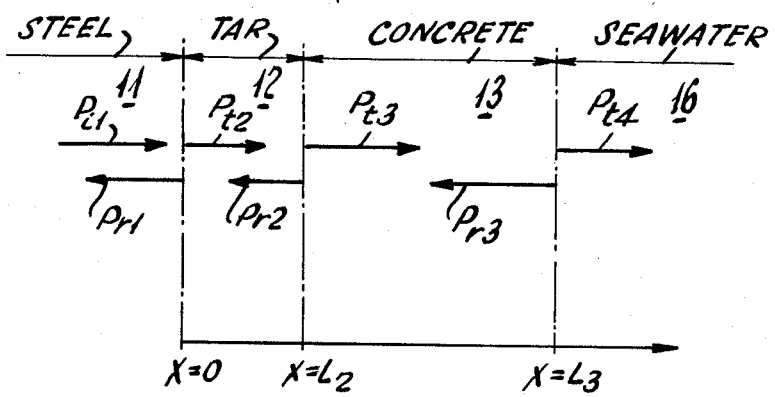
FIG. 1 is a diagram illustrating the principles of acoustic plane wave theory to the passage of an acoustic plane wave from a steel substrate through a layer of tar and concrete into sea water.

In order to illustrate the principles of the invention, reference may be had to FIG. 1. There is schematically indicated a substrate 11 (steel) through which a plane acoustic pressure wave passes. Such pressure wave is designated by an arrow labeled $P_{i1}$. There are two coating layers 12 and 13 on the substrate 11. As indicated by the captions, the layer 12 is tar while the layer 13 is concrete. Bordering the concrete layer 13 on the other side thereof is sea water 16.

In considering the principles as applied to the model illustrated by FIG. 1, the plane wave indicated by the arrow designated $P_{i1}$ transmits a pressure wave into the tar layer as indicated by the arrow designated $P_{i2}$. And, it will continue so as to pass a pressure wave into the concrete 13, as indicated by the arrow $P_{i3}$. Finally it will continue on into the sea water 16, as indicated by the arrow $P_{i4}$. At the same time there are reflections from the boundaries, as indicated by the arrows $P_{r1}$, $P_{r2}$ and $P_{r3}$. These are the reflected pressure waves from the boundaries between the substrate 11 and the coating layers 12 and 13, as well as the boundary between the coating layer 13 and the sea water 16.

By applying principles of acoustic plane wave theory to the model illustrated by FIG. 1, a transmission coefficient ($\alpha_T$) may be determined in terms of the characteristic impedances, wave numbers and thicknesses of the media making up the substrate, the coating layers and the sea water. Then by applying arbitrary dimensions for the thicknesses of the substrate layer 11 and the coatings 12 and 13 as well as the sea water 16, the transmission coefficient may be determined numerically for a range of frequencies, i.e. 20–120 KHz. For the purpose of making such numerical determinations the following table of parameter values were employed.

TABLE I

| PARAMETERS USED IN CALCULATIONS | | |
|---|---|---|
| | Acoustic | |
| Material | Velocity cm/sec | Impedance gm/cm² sec |
| steel | $5.9 \times 10^5$ | $4.565 \times 10^6$ |

TABLE I-continued

| PARAMETERS USED IN CALCULATIONS | | |
|---|---|---|
| | Acoustic | |
| Material | Velocity cm/sec | Impedance gm/cm² sec |
| tar | $2.314 \times 10^5$ | $3.52 \times 10^5$ |
| concrete | $3.1 \times 10^5$ | $8.1 \times 10^5$ |
| sea water | $1.50 \times 10^5$ | $1.535 \times 10^5$ |

Numerical determinations according to the above are illustrated by the curves of FIGS. 2, 3, 4, 5 and 6. Thus, a curve 17 represents the numerical determinations of the transmission coefficient ($\alpha_T$) as the ordinate, and the frequency as the abscissa, over the range of 20–120 KHz as illustrated in FIG. 2. It will be noted that the curve 17 indicates maxima for $\alpha_T$ on the curve at locations 20, 21, 22 and 23. These are the result of the numerical evaluation using a thickness of 1.6 cm of tar with a coating of 5.0 cm of concrete. Similarly in FIG. 3, there is a curve 26 that has maxima 27, 28 and 29 for the transmission coefficient $\alpha_T$. This curve represents determinations made over the same frequency range of 20–120 KHz using thicknesses of 1.6 cm of tar and 4.0 cm of concrete. FIG. 4 represents the same kind of numerical determinations for thicknesses of 1.6 cm of tar and 3.0 cm of concrete. In this case it produces a curve 32 with maxima 33, 34 and 35. In FIG. 5, the result is a curve 38 which has maxima 39 and 40 which results when the tar thickness is 1.6 cm and the concrete layer is 2.0 cm. Finally, FIG. 6 shows a solid line curve 44 and a dashed line curve 45. These represent the numerical determinations for layers of tar only. The curve 44 represents determinations where the layer was 1.6 cm of tar only, and the curve 45 represents determinations where the layer was 1.1 cm of tar only. It may be noted that the curve 44 has 2 maxima 47 and 48 while the curve 45 has 1 maximum 49. Both curves cover the frequency range of 20–120 KHz.

From the foregoing relationships, it was discovered that relating the combined thickness of tar and concrete to the average acoustic wave length of the tar and concrete layers at the frequencies covered, produced the maximum transmissions at approximately odd multiples of ¼ wavelength. A confirmation of the discovery is illustrated in the following Table II wherein the combined thickness of tar and concrete is represented by the symbol $d_T$ and the wavelength is represented by the symbol $\lambda$.

TABLE II

| Ratio $d_T/\lambda$ for successive maxima of $\alpha_T$ | | |
|---|---|---|
| $\alpha_{Tmax}$ | $d_T/\lambda$* | $d_T/\lambda$** |
| 1st | .755 ± .04 | .23 |
| 2nd | 1.27 ± .05 | .77 |
| 3rd | 1.74 ± .06 | |
| 4th | 2.22 | |

*$d_{tar}$ = 1.1 & 1.6 cm, $d_{concr.}$ = 5; 4; 3; 2 cm
**$d_{tar}$ = 1.1 & 1.6 cm, $d_{concr.}$ = 1; 0 cm It may be noted that the second column of the Table shows that the first maximum of the transmission coefficient ($\alpha_T$ max) occurs at ¾ wavelength, the second at 5/4 wavelength, the third at 7/4 wavelength and the fourth at 9/4 wavelength. This bears out the proposition that the i th maximum occurs at (2i+1)/4 wavelength for concrete thicknesses of 5, 4, 3, 2 cm and tar layers of 1.1 and 1.6 cm. And the third column shows that for concrete layers of 1 and 0 cm, with tar layers of 1.1 and 1.6 cm, the first maximum occurs at ¼ wavelength and the second at ¾ wavelength.

From the foregoing it will be appreciated that a determination may be made as to which of the frequencies, over the range considered, will produce maxima of acoustic energy transmission at particular thicknesses of the layers being penetrated by the acoustic energy. This is illustrated in FIG. 7 which shows concrete thickness as the ordinate and frequency as the abscissa. Solid line curves 53, 54 and 55 represent the frequencies at which the odd quarter wavelength maxima will occur for a given concrete layer thickness when the tar layer is 1.6 cm thick. Also, an additional curve 56 represents the frequencies for thin concrete layers (about one cm or less) that produce a one quarter wavelength maximum. Similarly, the dashed line curves 60, 61 and 62 represent the same thing when the tar layer has a thickness of 1.1 cm. From the foregoing it can be shown that, for example, if the concrete layer is 3.5 cm thick (broken line 63) with a layer of tar 1.6 cm the maxima at the odd multiples of ¼ wavelength, will occur at approximately 43, 70 and 94 KHz.

It will be understood that while the curves were developed for tar and concrete layers only, similar relationships which could be set forth might include taking into account the steel pipe wall thickness as well. Also it may be noted that the abbreviations used throughout the specification are well known, e.g. cm stands for centimerter(s) KHz stands for kilohertz and psi stands for pounds per square inch.

In accordance with the foregoing, and with reference to FIGS. 8 and 9, there is a pipeline survey instrument illustrated which may be employed to measure the thickness of a concrete coating on a subsea pipeline. The instrument makes use of a probe 64 which may be constructed like that described in a U.S. Pat. No. 4,202,216 issued May 13, 1980. As indicated in that patent, the probe 64 is designed for use on a pipeline inspection vehicle (not shown) commonly called a "pig."

FIG. 8 illustrates, in fragmentary cross section, a pipe wall 65 which has a coating of tar 66 and a relatively thick coating of concrete 67 there over. There is a wheel 70 that is part of the probe 64. Wheel 70 is mounted on a hollow shaft 71 and the wheel 70 is supported for rotation about its axis by elements 74 and 75. The elements 74 and 75 are carried by the remainder (not shown) of the probe 64. There are acoustic transducers 78 and 79 mounted in the wheel 70, and each transducer has an electrical circuit connection 80 and 81 respectively. The latter are for use in carrying out a concrete thickness measurement according to the invention.

The transducers 78 and 79 are preferably piezoelectric crystals. Transducer 78 may be employed as the transmitting crystals for generating the acoustic energy signals that are transmitted through the pipe wall 65 and the layer of tar 66 plus the concrete coating 67. It will be understood that in this example the concrete layer 67 is surrounded by sea water (not shown in FIG. 8) as has been indicated by the FIG. 1 schematic, so that the acoustic signals will continue on into the surrounding sea water.

The transducer 79 is employed as a receiving piezoelectric crystal. Its electrical signals are generated by the reflected acoustic energies being returned from the boundaries between the pipe wall 65 and the tar layer 66, plus the boundary between the tar layer 66 and the concrete coating 67 and also between the outer surface of the concrete coating 67 and the sea water beyond.

An electrical and/or electronic package is mounted on the probe 64 so as to operate with the acoustic trnsducers 78 and 79 and to process the acoustic information into thickness of the concrete coating 67. At the same time, because the probe 64 is on a pipeline pig there will be data concerning the position along the pipeline, and everything may be recorded on suitable mass storage equipment (as indicated in FIG. 9) for retrieval at the end of an inspection run.

Elements of the electronic package are illustrated in FIG. 9. Circuit connection 80 leads to the transducer 78 (FIG. 8). That transmitting piezoelectric crystal 78 has electrical signals applied thereto which are developed by a voltage controlled oscillator 86. Oscillator 86 develops the desired frequency sweep, e.g. from 20–120 KHz and these signals are transmitted over an output circuit connection 87 and via a driver amplifier 88 to energize the transducer 78. At the same time the circuit connection 81 (shown in FIG. 9) carries signals that are generated by the transducer 79 (FIG. 8). Such signals are generated by the reflected acoustic energies being returned (over the whole sweep of frequencies). These signals go to a wide band amplifier 91.

There is a microprocessor 92 which develops a control voltage for the voltage controlled oscillator 86. That control voltage goes via the circuit connection 93, to and from a digital-analog converter 95 and via another circuit connection 94 to the oscillator 86. The microprocessor 92 is programmed so as to cause the frequency controlled oscillator 86 to sweep over the desired frequency range e.g. 20 to 120 KHz.

The reflected acoustic energy signals that are generated by the transducer 79 (FIG. 8) are introduced to the microprocessor 92 via the circuit connection 81 and the wide band amplifier 91 to an analog-digital converter 96. From there the signals go to the microprocessors 92 via a circuit connection 97.

There is also another circuit from the output of the driving amplifier 88 in addition to that which energizes the transmitting transducer 78. It goes via connections 100 and 101 to another analog-digital converter 102. The output of converter 102 goes to the microprocessor 92 via a connection 105.

It may be noted that there are meters 108 and 109 which provide outputs representing the root mean square (RMS) of each of the received reflected signals and the transmitted frequency sweep signals, respectively. These DC voltages (representing the RMS voltage amplitudes) are fed respectively to the analog-digital converters 96 and 102, the outputs of which go to the microprocessor 92. Also there is a circuit connection 114 from the oscillator 86 to the microprocessor 92 so that in the microprocessor the ratio of the reflected signals (output of converter 96) to the transmitted sweep signals (output of converter 102) may be determined as a function of the oscillator frequency. Such ratio taken over the sweep of frequencies is reviewed under a program control in the microprocessor 92. Consequently the frequencies of minimum reflection, or maximum transmissibility are determined over the frequency range applied.

From the pattern of transmissibility maxima, the concrete layer thickness is determined in accordance with the above explanations. It may be done by calculations and/or by employing look up tables derived from calculations and experimental calibrations. The latter being stored in ROM of the microprocessor. In such manner, concrete thickness determinations are carried out and may be stored for later retrieval along with the portions of the pipeline surveying instrument. Thus, as indicated in FIG. 9, there is provision for position information to be introduced to the microprocessor via an input connection 117 indicated. Also, in relation to the microprocessor, there is an information storage element 120 for mass storage (as indicated above) and there may be a display element 121 for the data.

FIG. 10 illustrates a modification of the electrical and/or electronic package illustrated in FIG. 9. The modified arrangement may be employed to increase the reliability, and the signal to noise ratio of the measurements. In FIG. 10 the elements which are also found in FIG. 9 are designated by the same reference number but with a prime mark added. Thus, in FIG. 10 the voltage controlled amplifier 86' has its output modulated with a 20-30% amplitude of low frequency e.g. about 1 KHz. There is a low frequency oscillator 124 that is connected to a constant fraction multiplier 125. Multiplier 125 has an output of the voltage controlled oscillator 86' fed into it via a circuit connection 126 along with the output of the low frequency oscillator 124 via a circuit connection 127.

In the modified system the driver amplifier 88' also acts as a modulator and the output of the driving amplifier 88' carries the modulated frequency sweep signals over the circuit connection 80' which goes to the transmitting transducer 78 (FIG. 8). In addition there is a demodulator 130 and a band pass amplifier 131 plus a rectifier 132, all three of which replace the meter 109 of the FIG. 9 circuit. Therefore the amplitude of the demodulated frequency sweep signals go to the analog-digital converter 102' and to the microprocessor 92'.

On the receiver side (connection 81') of the FIG. 10 circuit, there is a demodulator 135 and a band pass filter and amplifier 136 followed by a rectifier 137. These transmit the reflected signals received by the transducer 79 (FIG. 8) via the circuit connection 81' to the analog-digital converter 96'. Then the signals are handled by the microprocessor 92' in like manner as described above in connection with the FIG. 9 modification. The FIG. 10 modification manner of handling the signals will reduce the noise and other interference.

It will be appreciated by anyone skilled in the art that there are various microprocessors and/or computers available which may be employed as the microprocessor unit 92 (and 92') illustrated in FIGS. 9 and 10. For example, there are two models of a microprocessor/computer manufactured by Hewlett-Packard designated HP 9826 and HP 9836 which would be satisfactory. Similarly, in respect to the other elements of the systems illustrated in FIGS. 9 and 10, the digital to analog converter 95 may be a Hewlett-Packard D/A converter designated HP 59313A. And, the analog-dital converters 96 and 102 may be both together a Hewlett-Packard unit designated A/D Converter (Four channel) HP 59313A. Likewise, the voltage controlled oscillator 86 may be a Hewlett-Packard unit designated VCO HP 3311A. The power amplifier 88 may be one manufactured by Bruel & Kjaer Instrument Inc. of Marlborough, Mass. designated as Power Amplifier type 2713. Likewise, the amplitude measuring meters 108 and 109 may be measuring amplifiers along with Bruel & Kjaer meters designated RMS Meter Type 2610. The amplifier 91 may be a Bruel & Kjaer preamplifier designated as Charge Preamplifier Type 2634 or 2651.

While a particular embodiment of the invention has been described above in considerable detail in accordance with the applicable statutes, this is not to be taken as in any way limiting the invention but merely as being descriptive thereof.

I claim:

1. Method of determining the thickness of a coating layer on a substrate, comprising the steps of
   transmitting acoustic energy through said substrate and coating layer transversely to said coating layer,
   sweeping the frequency of said transmitted acoustic energy over a predetermined range of frequencies,
   receiving reflected acoustic energy from the boundaries between said substrate and coating layer and between said coating layer and beyond, and
   determining the frequencies at which minimum acoustic energy transmissions occur whereby said coating layer thickness is determined.

2. System for determining thickness of a layer of coating on a substrate, comprising in combination
   means for transmitting a predetermined range of frequencies of acoustic energy through said substrate and coating,
   means for receiving reflections of said transmitted range of acoustic energy,
   means for determining the amplitude of said reflections over said predetermined range of frequencies whereby said coating thickness is determined from the transmissibility pattern over said frequency range.

3. System according to claim 2, wherein
   said means for transmitting comprises a first transducer and means for energizing said transducer by sweeping it with said predetermined range of frequencies,
   said means for receiving comprises a second transducer for generating signals over said predetermined range of frequencies, and
   said means for determining comprises means for measuring the amplitude of said generated signals.

4. System according to claim 3, wherein said means for energizing said first transducer comprises a variable frequency oscillator.

5. System according to claim 4, wherein said variable frequency oscillator is voltage controlled.

6. System according to claim 5, wherein said means for determining comprises a microprocessor.

7. System for determining thickness of a layer of coating on a substrate, comprising in combination
   a first piezoelectric transducer for transmitting a range of frequencies of 20-120 KHz of acoustic energy through said substrate and coating,
   a voltage controlled variable frequency oscillator and first circuit means for introducing a voltage to sweep said oscillator over said range of frequencies and for connecting said oscillator to energize said first transducer,
   a second piezoelectric transducer for receiving reflections of said transmitted range of acoustic energy and for generating signals in accordance therewith, and
   second circuit means comprising a microprocessor for determining the amplitude of said reflection signals whereby said coating thickness is determined from the transmissibility pattern over said frequency range.

8. Method of measuring thickness of a concrete layer on a subsea pipeline, wherein said pipeline includes a pipe coated with a layer of concrete, comprising transmitting a frequency sweep of acoustic energy through a wall of said coated pipe, receiving reflected acoustic energy returned over said frequency sweep, and determining the acoustic transmissibility through said wall of coated pipe over said frequency sweep whereby said concrete layer thickness is determined.

9. Method according the claim 8, wherein said step of determining the acoustic transmissibility, comprises measuring the amplitude of said transmitted energy over said frequency sweep, measuring the amplitude of said reflected energies, and determining the ratio of said reflected energies to said transmitted energy as a function of said frequencies whereby the pattern of minimum reflection frequencies indicate said concrete layers thickness.

10. System for measuring thickness of a coating on a pipe, comprising in combination means for transmitting a frequency sweep of acoustic energy through a wall of said pipe, means for receiving reflected energy from said transmitted sweep, and means for determining the transmissibility of said acoustic energy over said frequency sweep whereby said coating thickness is determined.

11. System according to claim 10, wherein, said transmitting means comprises a first acoustic transducer, and electronic circuit means for energizing said transducer with said sweep of frequencies, said receiving means comprises a second acoustic transducer, and means for amplifying signals generated by said second acoustic transducer over said sweep of frequencies, and said determining means comprises a microprocessor.

12. System according to claim 11 wherein said determining means also comprises (1) means for measuring the amplitude of said first transducer energizing signals over said sweep of frequencies, (2) means for measuring the amplitude of said second transducer generated signals over said sweep of frequencies; and (3) means for determining the ratio of said amplitudes of signals (1) to the amplitudes of signals (2) as a function of the individual frequencies over said sweep of frequencies.

13. System for measuring thickness of a concrete coating on a subsea pipeline, comprising in combination a first piezoelectric transducer adapted for transmitting a sweep of acoustic energy over a range of 20–120 KHz through the wall of said pipe and concrete coating into said sea, a second piezoelectric transducer adapted for receiving said sweep of acoustic energy reflected from the boundaries of said pipe wall and concrete coating, first circuit means for energizing said first transducer, second circuit means for amplifying signals generated by said second transducer, a variable frequency oscillator for generating a sweep of frequencies over said range of 20–120 KHz, third circuit means for connecting the output of said oscillator to said first transducer, means for measuring the amplitudes of said transmitted and received acoustic energies, a microprocessor;

fourth circuit means for connecting said microprocessor to control said oscillator, and fifth circuit means for connecting said amplitude measuring means to said microprocessor whereby the ratio of said measured amplitudes over said range of frequencies is determined and the thickness of said concrete coating measured.

* * * * *